United States Patent [19]

Nowakowski

[11] Plant 4,074

[45] July 12, 1977

[54] VARIEGATED PIGGY-BACK PLANT

[76] Inventor: Richard Joseph Nowakowski, 2560 Ridgeway Drive, National City, Calif. 92050

[21] Appl. No.: 712,031

[22] Filed: Aug. 5, 1976

[51] Int. Cl.[2] ..... A01H 5/12

[52] U.S. Cl. ..... Plt./88

[58] Field of Search ..... Plt./88

*Primary Examiner*—Robert E. Bagwill
*Attorney, Agent, or Firm*—Brown & Martin

[57] ABSTRACT

A new variety of the foliage plant *Tolmiea menziesii*, commonly known as the piggy-back plant, is characterized by variegated leaves.

2 Drawing Figures

The present invention relates to a new and distinct variety of *Tolmiea menziesii*, commonly known as the piggy-back plant, a remarkable foliage plant which produces a new plantlet on its leaves, hence the name "Piggy-Back". The parent of my new variety was the plant *Tolmiea menziesii*. This plant is native to coastal mountain ranges from Northern California northward to Alaska. The leaves of the parent are substantially heart-shaped, fern green with delicate fuzz and toothed edges. New plantlets grow on top of old leaves. The plant produces inconspicuous, reddish brown flowers, and thrives in filtered light, cool temperatures and plenty of moisture.

BRIEF DESCRIPTION OF THE DRAWING

My new plant can be best understood from the following description when read in conjunction with the drawing wherein.

DETAILED DESCRIPTION OF THE PLANT

My new invention is a mutation, which was originated by me, in my propagating bed. One plant came up in the bed with a variegated leaf. I asexually propagated the leaf as a cutting and got a beautiful variegated plant, the leaves of which were spotted and blotched with various shades of yellow. I grew this plant for approximately one year's time and further propagated the plant. The variegation of the leaves has proved to hold from generation to generation, thus originating a new variety of the species.

Asexual propagation (reproduction) of this variety is necessary as it comes from a monotypic genus, only one species is listed.

The following is a detailed description of my new variety, as based upon specimens grown at my nursery in National City in Southern California. Color terminology in accordance with Exotica Horticultural Color Guide. Determinations approximate Maerz and Paul "Dictionary of Color", cited by the National Bureau of Standards and the Royal Horticultural Society of Color Charts.

The plant is a foliage plant, of a hardy, vigorous variety, characterized by clusters of variegated leaves, adventitious buds usually occur in the sinuses of the leaf blades, forming new plants with age. Maximum height 12–18″. A remarkable house or patio plant, well suited to shady areas.

Leaves: on petioles 2–12″ long, according to the amount of light given, length may vary.

The blades are pubescent, cordate, lobed, irregularly heart shaped and toothed, one to five inches across.

Color: the color of the leaves is the remarkable feature of the plant. The leaves are fern green, blotched and speckled with various shades of yellow and yellow-green. At first appearance, the leaves are greenish, but with age, speckles of chartreuse appear, becoming more and more pronounced with cream, mimosa and canary yellow, at various stages of leaf growth. These various stages are clearly shown in FIG. 1.

Figure 1:
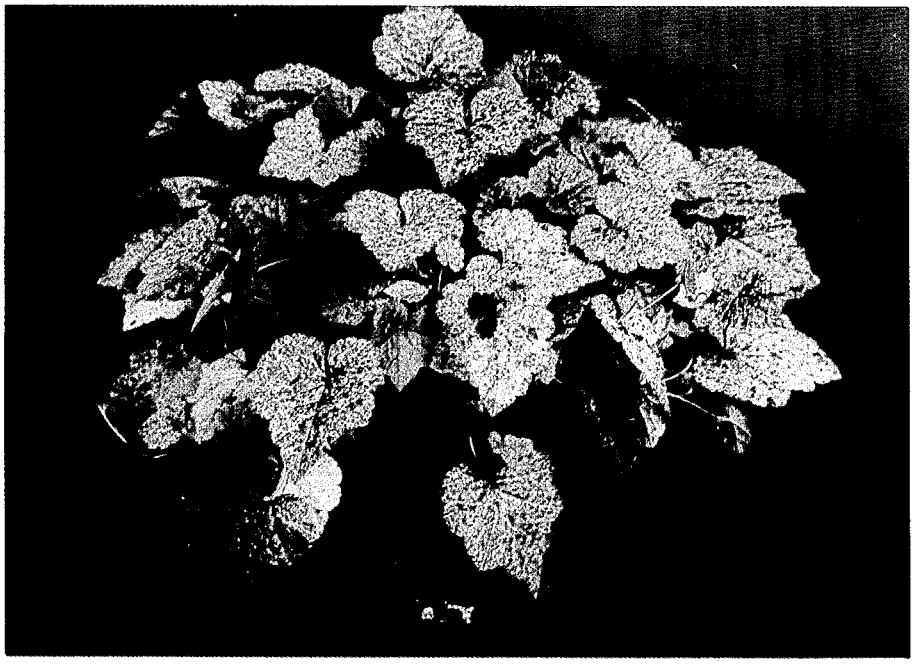
FIG. 1 is a color photograph of the plant taken from the side and slightly above.

For example, a new leaf (fern green in color) is shown growing out of a variegated leaf of advanced age in approximately the center of the photo of FIG. 1. The variegated leaf is shown splotched with colors including fern green, chartreuse, shades of yellow and splotches of almost white.

An aged leaf, faded in color to almost white is shown in the lower left of the plant partially hidden behind two other leaves, both of different shades of color.

Figure 2:
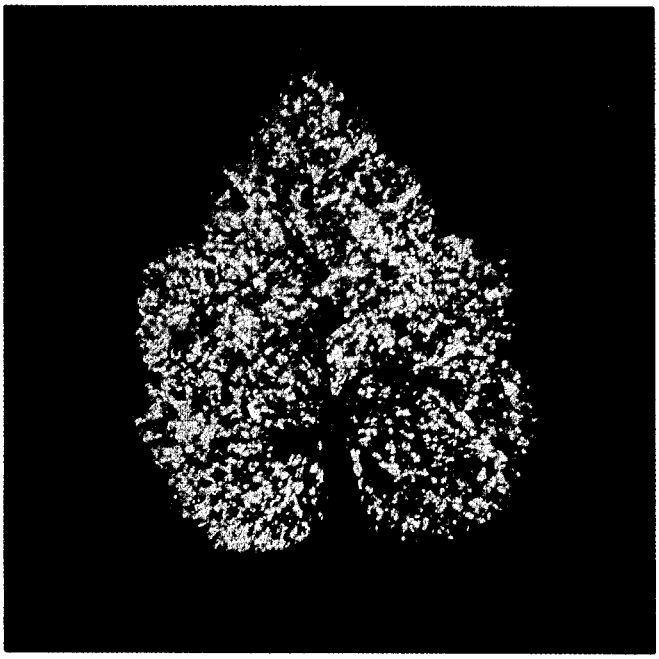
FIG. 2 is a plane view photographed in color of a typical leaf of the plant of FIG. 1.

The FIG. 2 photograph shows a single leaf illustrating the substantially heart shape, and toothed edges of the leaves. The range of colors of a mature leaf is also clearly brought out.

Flowers: insignificant, in a raceme on a stem 1 to 3 feet tall, purplish calyx has five unequal lobes slit on one side.

Use: primarily a foliage type plant only, ornamental.

I claim:

1. A new and distinct variety of piggy-back plant (*Tolmiea menziesii* variety variegata) substantially as herein shown and described, characterized particularly as to the novel variegated foliage, a new and vigorous decorative type plant.

* * * * *